United States Patent [19]

Milder

[11] Patent Number: 5,281,215
[45] Date of Patent: Jan. 25, 1994

[54] CRYOGENIC CATHETER

[75] Inventor: Fredric L. Milder, Brookline, Mass.

[73] Assignee: Implemed, Inc., Brookline, Mass.

[21] Appl. No.: 898,142

[22] Filed: Jun. 15, 1992

Related U.S. Application Data

[63] Continuation-in-part of Ser. No. 870,495, Apr. 16, 1992.

[51] Int. Cl.$^5$ .................................. A61B 17/36
[52] U.S. Cl. .................................. 606/20; 606/21; 606/23; 606/25
[58] Field of Search .................................. 606/20-26

[56] References Cited

U.S. PATENT DOCUMENTS

| | | | |
|---|---|---|---|
| 3,272,203 | 9/1966 | Chato | 606/21 X |
| 3,393,679 | 7/1968 | Crump et al. | 128/303.1 |
| 3,425,419 | 2/1969 | Dato | 128/400 |
| 3,512,531 | 5/1970 | Crump et al. | 128/303.1 |
| 3,524,446 | 8/1970 | Crump et al. | 606/25 |
| 3,548,829 | 12/1970 | Reynolds et al. | 128/303.1 |
| 3,664,344 | 5/1972 | Bryne | |
| 3,823,718 | 7/1974 | Tromovitch | |
| 3,859,986 | 1/1975 | Okada et al. | |
| 3,910,277 | 10/1975 | Zimmer | |
| 3,948,269 | 4/1976 | Zimmer | 606/24 |

(List continued on next page.)

FOREIGN PATENT DOCUMENTS

| | | |
|---|---|---|
| 2613778 | 10/1977 | Fed. Rep. of Germany .......... A61B 17/36 |
| 2731651 | 1/1979 | Fed. Rep. of Germany . |
| 2477406 | 9/1981 | France . |
| WO8600232 | 1/1986 | PCT Int'l Appl. . |
| 532976 | 11/1978 | U.S.S.R. . |

OTHER PUBLICATIONS

The annals of Thoracic Surgery—"Surgical Repair of Wolff-Parkinson-White Syndrome: A New Closed-Heart Technique" by Gerard M. Guiraudon, M.D., et al., vol. 37, No. 1, Jan. 1984, pp. 67-71.

The Journal of Thoracic and Cardiovascular Surgery—"Transannular Cryoablation of Ventricular Tachycardia" by Gerald M. Lawrie, M.D., et al., vol. 98, No. 6, Dec. 1989.

European Heart Journal (1988) "Cryosurgery for Ventricular Bigeminy Using a Transaortic Closed Ventricular Approach" by F. E. E. Vermeulen, et al., pp. 979-990.

"Transvenous Cryoablation of the Bundle of HIS" by Paul C. Gillett, et al., vol. 14, Apr. 1991, pp. 504-510.

Primary Examiner—Peter A. Aschenbrenner
Attorney, Agent, or Firm—Weingarten, Schurgin, Gagnebin & Hayes

[57] ABSTRACT

The invention provides a catheter for ice mapping and ablation and a method of ablation using the catheter. The catheter includes at least two lumens for circulating a refrigerating fluid adjacent an ablation device located at the end of a catheter. The refrigerated ablation device is used to chill a localized region of myocardial tissue, thereby permitting the resulting change in electrical activity to be determined. In response to the test results, the ablation device may be used to make a lesion in the myocardial tissue to correct a cardiac arrhythmia. In one embodiment, the ablation device is an electrode which uses radio frequency energy to ablate the myocardial tissue. Alternatively, the ablation device is an electrode adapted for direct current ablation. In another embodiment, the electrode is replaced with an optical fiber in communication with a laser which uses the laser's light energy to ablate tissue. Yet another embodiment is a cryogenic catheter, useful for cooling tissue for other applications, for use as combined or separate mapping and ablation devices, or for use with the ice mapping and ablation means of the present invention. The embodiments may include provisions for steering the catheter and for stabilizing the ablation device at the proposed lesion site.

16 Claims, 6 Drawing Sheets

U.S. PATENT DOCUMENTS

| | | |
|---|---|---|
| 3,971,383 | 7/1976 | van Gerven . |
| 4,022,215 | 5/1977 | Benson .................. 606/21 X |
| 4,029,102 | 6/1977 | Barger . |
| 4,275,734 | 6/1981 | Mitchiner . |
| 4,278,090 | 7/1981 | van Gerven . |
| 4,377,168 | 3/1983 | Rzasa et al. ............ 606/26 X |
| 4,406,656 | 9/1983 | Hattler et al. . |
| 4,519,389 | 5/1985 | Gudkin et al. . |
| 4,601,705 | 7/1986 | McCoy .................... 604/95 |
| 4,641,649 | 2/1987 | Walinsky et al. ........ 606/33 |
| 4,770,171 | 9/1988 | Sweren et al. .......... 606/25 |
| 4,819,630 | 4/1989 | De Hart .................. 606/15 |
| 4,832,024 | 5/1989 | Boussignac et al. .... 606/15 X |
| 4,860,744 | 8/1989 | Johnson et al. . |
| 4,899,741 | 2/1990 | Bentley et al. ......... 606/27 |
| 4,934,340 | 6/1990 | Ebling et al. ........... 604/95 X |
| 5,041,973 | 8/1991 | Lebrow et al. ......... 128/642 X |
| 5,056,517 | 10/1991 | Fenici ..................... 128/786 X |
| 5,108,390 | 4/1992 | Potocky et al. ........ 606/21 |
| 5,147,355 | 9/1992 | Friedman et al. ...... 606/23 |
| 5,151,096 | 9/1992 | Khoury ................... 606/17 X |
| 5,161,539 | 11/1992 | Evans et al. ............ 128/700 X |

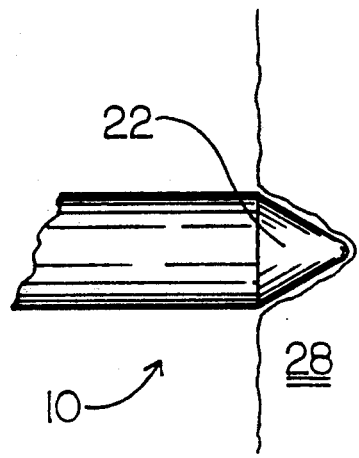
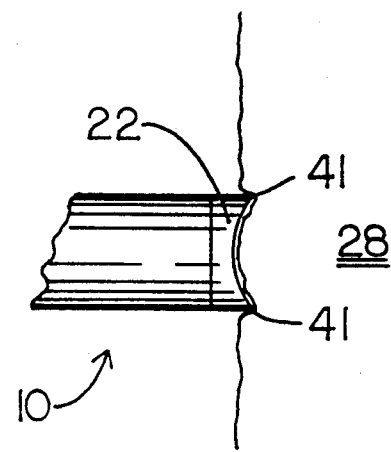
FIG. 7                    FIG. 8
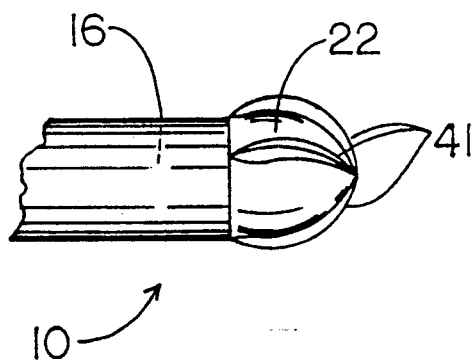
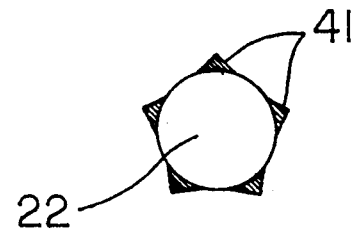
FIG. 9                    FIG. 10

5,281,215

CRYOGENIC CATHETER

RELATED INVENTION

This application is a Continuation-in-Part of U.S. patent application Ser. No. 07/870,495, filed Apr. 16, 1992 (Our File No. MSPI-002XX).

FIELD OF THE INVENTION

The invention relates to the field of catheters, and more particularly to a catheter used in cardiac procedures.

BACKGROUND OF THE INVENTION

Cardiac arrhythmias are caused by localized electrophysiologic phenomena. These are of generally two types: additional foci or reentrant circuits. Reentrant circuits can be highly localized, as in ventricular tachycardia postinfarction or AV node reentry, or can be of a grosser morphology, as in accessory pathway pathologies. Since they are localized phenomena, they can be treated surgically. The task is to remove or destroy the offending region, thereby eliminating the source of the arrhythmia.

Current surgical therapies include: cardiotomy; open chest cryoablation; closed-chest catheter radio frequency (rf) ablation; and closed-chest direct current ablation. Radio frequency catheter ablation is becoming the therapy of choice. The greatest drawback of rf ablation is that, prior to ablation, the site of the intended cardiac lesion must be determined by conventional electrocardiographic mapping. Unfortunately, conventional mapping does not provide definitive isolation of the problem area. In a great majority of cases, more than one lesion must be made in order to effect a cure. Multiple lesions are required because the effectiveness of each of the proposed lesion sites cannot be predetermined due to the limitations of conventional electrocardiographic mapping. Often five lesions, and sometimes as many as twenty lesions may be required before a successful result is obtained. Usually only one of the lesions is actually effective; the other lesions result in unnecessarily destroyed cardiac tissue.

Treatment of cardiac arrhythmias through selective ablation of cardiac tissue may be improved if, prior to ablation, the local electrical activity of the region can be suppressed to determine the effectiveness of the proposed lesion site in stopping the arrhythmia. Localized electrical activity may be suppressed by chilling small regions of myocardial tissue and then performing electrocardiographic mapping to evaluate the arrhythmia. This technique of cooling and mapping is called "zero-degree" or "ice" mapping. If the proposed lesion site would be effective, as determined by the ice mapping, to eliminate the arrhythmia, the site is ablated. Despite the advantages of cryoablation, it has not been the technique of choice for want of a single, easily operated device which effectively combines the functions of cryogenic cooling of cardiac tissue and tissue ablation.

SUMMARY OF THE INVENTION

The invention provides an ablation catheter which combines zero-degree or ice mapping and tissue ablation means in a single device. The invention includes a first and a second lumen for circulating a cooling fluid to the distal end of a catheter which includes an ablation device. The ablation device may be one pole of a multipole mapping electrode which conducts radio frequency energy, or direct current energy for tissue ablation. Alternatively, the ablation electrode may be replaced with an optical fiber in communication with a laser. The light energy is dispersed by a light diffuser toward a lesion site to ablate the tissue. The catheter may have an optional steering device to curve the distal end of the catheter, and the ablation device may be held in contact with the myocardial tissue with the aid of a pointed ridge.

Another feature of the invention is a method for ice mapping and ablation using the above-described catheter. The catheter is inserted through an artery or vein into the heart or into a cardiac vessel and placed against the site of a proposed lesion. Cooling fluid is circulated to the tip of the catheter through the lumens, thereby cooling a localized region of cardiac tissue. The electrical activity of the heart is then measured to evaluate the effectiveness of the proposed site. If the test results indicate that a lesion would eliminate a cardiac arrhythmia, the region is ablated with either radio frequency, direct current or laser light energy.

Yet another embodiment of the invention is a cryogenic device useful for cardiac cryosurgery, mapping, any endoscopic cryosurgery or as a cryoprobe in open surgical procedures. The invention provides a first lumen within a second lumen for circulating a pressurized refrigerant at a cooling tip. Flow control of the fluid is achieved through either a passive ball and spring device or an active, electric control valve.

BRIEF DESCRIPTION OF THE DRAWINGS

A more complete understanding of the present invention attendant advantages and features thereof will be more readily understood by reference to the following detailed description when considered in conjunction with the accompanying drawings wherein:

FIG. 7 illustrates an embodiment of a stabilization device having a point imbedded in cardiac tissue to temporarily anchor the ice mapping and ablation catheter at a desired location;

FIG. 8 illustrates another embodiment of a stabilization device having a concave electrode or ablation tip with a ridge on its perimeter;

FIG. 9 illustrates another embodiment of a stabilization device which incorporates a series of longitudinal ridges on the tip of the catheter;

FIG. 10 is a cross-sectional view of the tip illustrated in FIG. 9, which more clearly illustrates the location and shape of the ridges;

DETAILED DESCRIPTION OF THE INVENTION

Figure 1:
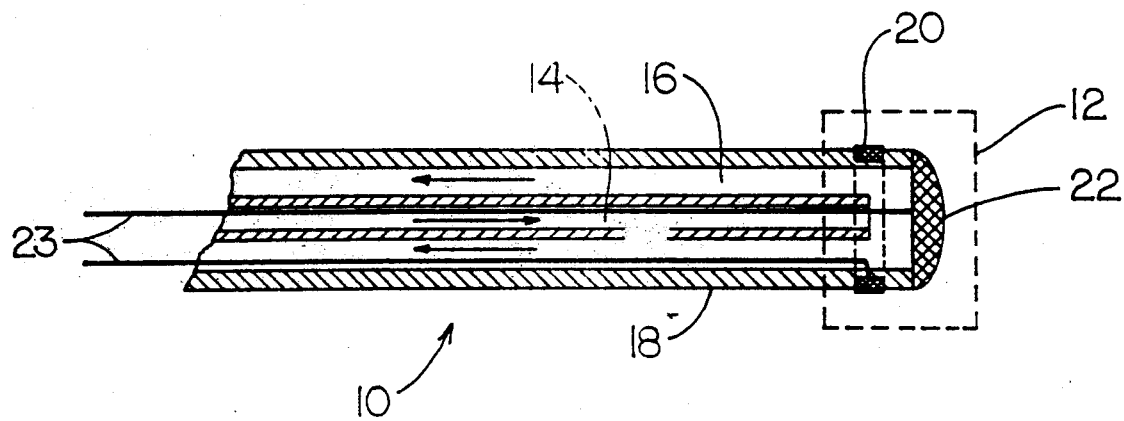
FIG. 1 is a schematic of an embodiment of the catheter of the invention for ice mapping and ablation, having mapping electrodes and a first rf ablation electrode at the distal end of the catheter.

FIG. 1 is a schematic of an embodiment of the ice mapping and ablation catheter 10. The catheter 10 has a tip 12 at its distal end which is alternately used for ice-mapping and radio frequency ablation. The proximal end of the catheter 10 is accessible to a surgeon and is connectable to a refrigerant source (not shown). The ice mapping and ablation catheter 10 combines two lumens 14 and 16 within the catheter body 18 to carry a refrigerant to and away from, respectively, the tip 12. The exemplary embodiment of the ice mapping and ablation catheter 10, depicted in FIG. 1, has the following wall dimensions for lumens 14 and 16: outer lumen 16, 0.117" Outer Diameter (O.D.) by 0.088" Inner Diameter (I.D.); and inner lumen 14, 0.068" O.D. by 0.060" I.D.

In the embodiment shown, the tip 12 includes a first electrode 20, circumferentially disposed on the catheter body 18, and a second electrode 22, both connected to an electrical signal amplifier with wires 23. The first and second electrodes 20 and 22 are used together to perform electrocardiographic mapping. The electrodes 20, 22 are made of an electrically conductive material such as copper, silver or aluminum, which is plated with gold, platinum or titanium. The second electrode 22 also acts as a thermal conductor between the catheter tip 12 and cardiac tissue when a refrigerant is passed through the inner lumen 14 to the tip 12. For radio frequency (rf) ablation, a wire 23 supplies (rf) current to the second electrode 22 which acts as an ablation device.

In other embodiments, additional electrodes may be added to the tip 12 to make a multipole mapping electrode. In another embodiment, a conductive refrigerant may be used to provide the electrical connection to the first electrode 20, thereby obviating the need for wires 23. In yet another embodiment, the refrigerant is an electrically insulating fluid like trimethylsiloxy terminated polydimethylsiloxane, and the wires 23, free of insulation, may be located within the lumens 14 and 16; one wire 23 in the inner lumen 14, and one wire 23 in the outer lumen 16. The combination of the insulating fluid and the insulating effect of the walls of the lumens 14 and 16 electrically isolate the wires 23 from each other.

In all of the embodiments, the ablation surface or device on the tip 12 is not necessarily the second electrode 22. The ablation device may be a separate surface which is distinguishable from the second electrode 22. In some embodiments, it may be desirable to entirely omit the first and second mapping electrodes 20 and 22 from the catheter 10, and to perform electrocardiographic mapping by other means, such as non-invasive cardiac monitoring.

Figure 2:
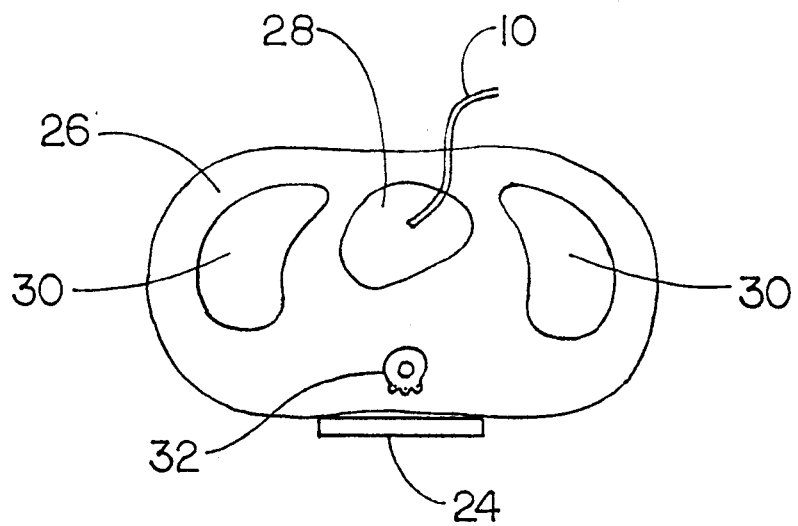
FIG. 2 is a cross-sectional view of a human body, showing a catheter of the invention within the heart and a second rf electrode beneath the body.
Figure 3:
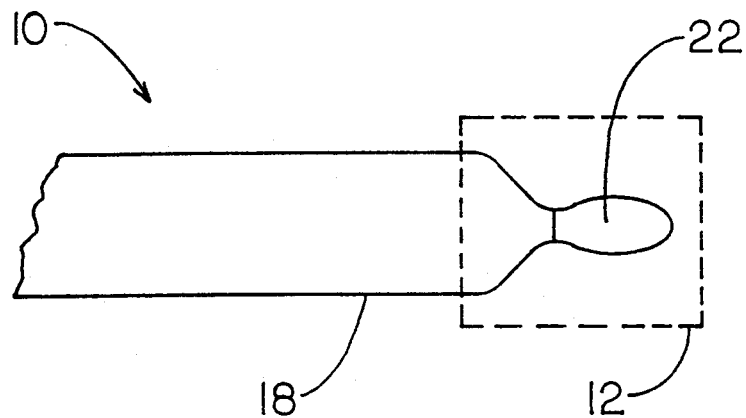
FIG. 3 is a side view of an embodiment of the catheter for ice mapping having an electrode for direct current ablation.

When the catheter 10 is used for ablation, the second electrode 22 and a third electrode 24, shown in FIG. 2, are employed. FIG. 2 is a representative cross-section of a human chest cavity 26 depicting approximate locations of a heart 28, lungs 30 and spinal column 32. The patient is shown resting on a conductive plate or third electrode 24. The ice-mapping and ablation catheter 10, which is smooth enough to pass easily through blood vessels and heart valves, is shown inside the heart 28. Creation of an electrical potential difference between the second electrode 22 and the third electrode 24 permits controlled ablation of cardiac tissue. The third electrode 24 may also be used for electrocardiographic mapping. In another embodiment of the catheter 10, shown in FIG. 3, a reconfigured tip 12 houses an elongated second electrode 22 useful for direct current ablation.

The catheter 10 of FIG. 1 is better understood with reference to its use in an operative procedure. Following the determination of a proposed lesion site by electrocardiographic mapping, using the first and second electrodes 20 and 22 with a method known in the art, the ice mapping and ablation catheter 10 is directed to the proposed region where lesions will be made. Following positioning of the tip 12 on the cardiac tissue, the refrigerant flow is turned on to allow a cooling fluid, such as ethyl alcohol, freon, or polydimethlsiloxane to flow from the reservoir within the inner lumen 14 to the tip 12, and then to return to the reservoir via the outer lumen 16. While the flow direction may be reversed, causing refrigerant to be introduced via the outer lumen 16 and withdrawn from the inner lumen 14, the resultant cooling of the exterior of the catheter body 18 would unnecessarily cool blood vessels and require that the refrigerant be colder when introduced into the catheter 10, to allow for warming of the coolant before it reaches the tip 12. In another embodiment of the catheter 10, the catheter body 18 may enclose a "bundle" of lumens as an alternative to the "tube-within-a-tube" configuration depicted in FIG. 1. In all of the configurations, circulation of refrigerant at the tip 12 permits controllable cooling of the tip 12 to cool the proposed lesion site.

Figure 4:
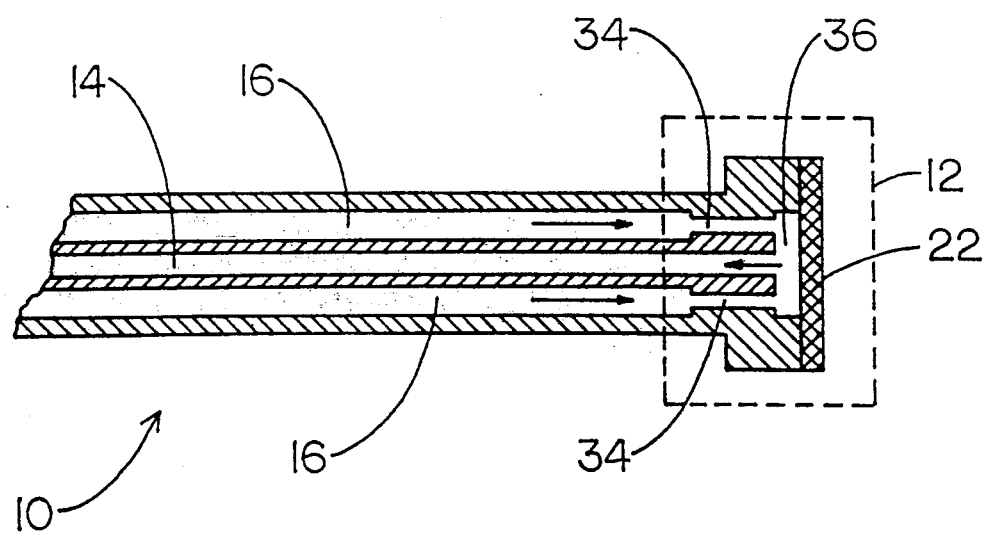
FIG. 4 is a schematic of an embodiment of the catheter for ice mapping and ablation having a tip which is cooled by gas expansion.

An alternative means of cooling the tip 12 is through gas expansion cooling by the Joule-Thompson effect, as is known in the art in cryoablation. A tip 12 configured for expansion cooling is shown in FIG. 4. The tip 12 has numerous small channels 34 which allow passage of a pressurized gas, such as nitrous oxide or carbon dioxide, from the outer lumen 16 into a gas expansion chamber 36. As the gas expands rapidly, it chills the thermally conductive electrode 22. The cold gas is then withdrawn from the tip 12 through the inner lumen 14. In lieu of pressurized gas, a liquid such as chlorodifluoromethane may be used for cooling. Liquids such as chlorodifluoromethane boil at a low temperature and cool by removing heat of vaporization through boiling.

Figure 5:
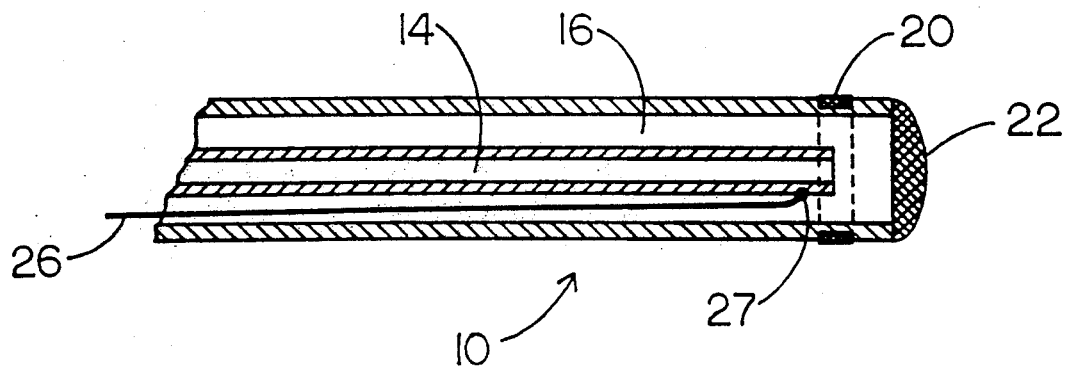
FIG. 5 is a schematic of an embodiment of the invention having a movable cable to permit steering of the catheter.

The exterior wall of the outer lumen 16 is the same surface as the exterior of the catheter body 18 and may include an internal metal braid to make the ice mapping and ablation catheter 10 torqueable for intracardiac manipulation. To further facilitate intracardiac manipulation, a cord, wire or cable 26 may be incorporated with, or inserted into, another lumen so as to make the ice mapping and ablation catheter 10 steerable. In the embodiment of FIG. 5, the cable 26 is attached to the inner lumen 14 at an attachment point 27 near the distal end of the inner lumen 14. When the surgeon tightens or pulls on the cable 26 the distal end of the inner lumen 14 moves within the outer lumen 16. As the distal end of the inner lumen 14 curves, it presses against the distal end of the outer lumen 16 and thereby causes the distal end of the catheter 10 to bend in proportion to the force applied to the cable 26. Conversely when the cable 26 is released, the curvature of the distal end of the catheter 10 is decreased.

Figure 6:
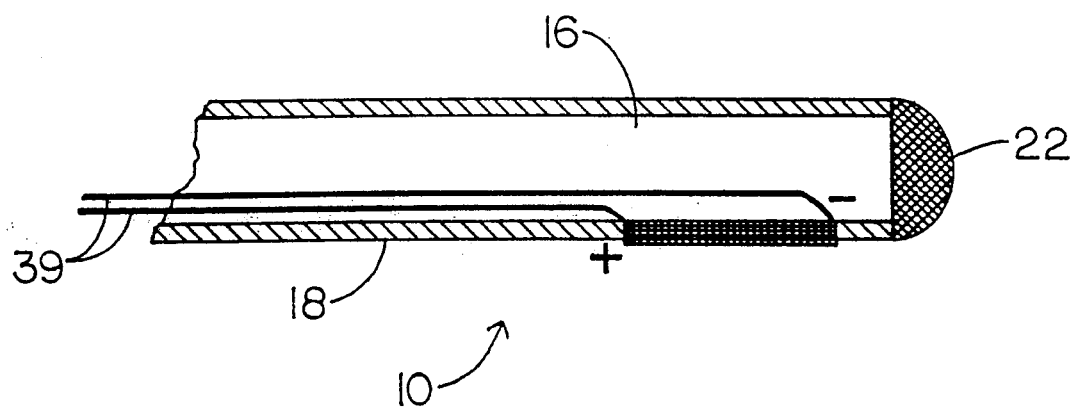
FIG. 6 is a schematic of an embodiment of the invention having a piezo-electric steering element within the catheter near the distal end.

It is further contemplated that a piezo-electric plastic, such as polyvinylidenefluoride (trade name Kynar ®), be added to the inner or outer surface of the distal end of either the inner lumen 14 or the outer lumen 16 to make the ice mapping and ablation catheter 10 similarly steerable. Referring to FIG. 6, a catheter 10 is shown with an approximately three centimeter Kynar ® segment 38 incorporated into a portion of the wall of the outer lumen 16 near the distal end of the catheter 10. The segment 38 has positive and negative electrical leads connected to an electrical power supply with wires 39. Application of an electric current of one polarity causes the segment 38 contract, which then causes the distal end of the outer lumen 16 to curve. Reversing the electrical polarity causes the segment 38 to expand, thereby causing the distal end of the outer lumen 16 to curve in the opposite direction. The movement of the outer lumen 16 causes a corresponding movement of the inner lumen 14 and permits controlled placement of the tip 12 against cardiac tissue.

It is further contemplated that a second segment 38 be incorporated into a wall portion of the outer lumen 16 opposite the first segment 38. Control of the distal end of the catheter 10 is achieved as with the single segment 38, except that voltages of opposite polarity are applied to the segments 38 simultaneously, thereby causing one segment 38 to contract and the other segment 38 to expand.

An ice mapping and ablation catheter 10, having the exemplary above-referenced wall dimensions and a length of 100 centimeters, requires refrigerant pressurization of approximately 200 pounds per square inch to produce a refrigerant flow of approximately 350 cc/min through the catheter 10. With a refrigerant inlet temperature of −60 degrees Celsius, a 350 cc/min flow, and a polyurethane wall material, the temperature of the tip 12 is approximately −10 degrees Celsius when the catheter body 18 is positioned inside a human body having a nominal temperature of 37 degrees Celsius. This temperature is sufficiently cold to do ice mapping.

The first step in the ice mapping procedure is placing the cooled tip 12 at the proposed lesion site. Because the operative procedure has several steps, the tip 12 must be stabilized at the proposed lesion site for the time necessary to ice map, to evaluate, and to ablate. A variety of configurations of the tip 12 may be employed to help secure or stabilize the catheter 10 in place against the myocardium. FIG. 7 depicts a pointed tip 12 or second electrode 22; FIG. 8 illustrates a concave tip 12 or second electrode 22 having lip or ridge 41; and FIG. 9 depicts a bulbous tip 12 having a series of ridges 41 on the side of the tip 12. FIG. 10 is a cross-sectional view of the tip 12 of FIG. 9, which more clearly illustrates the configuration of the stabilizing ridges 41.

When the cardiac tissue reaches approximately +5 degrees Celsius, its electrical activity is suppressed. If the proposed lesion site will be therapeutically effective when ablated, the arrhythmia will no longer be inducible once the electrical activity of the proposed site is suppressed by cooling. Having confirmed the effectiveness of the proposed site, rf ablation is performed using the second electrode 22 and the third electrode 24 in manner known to those skilled in the art.

Figure 11:
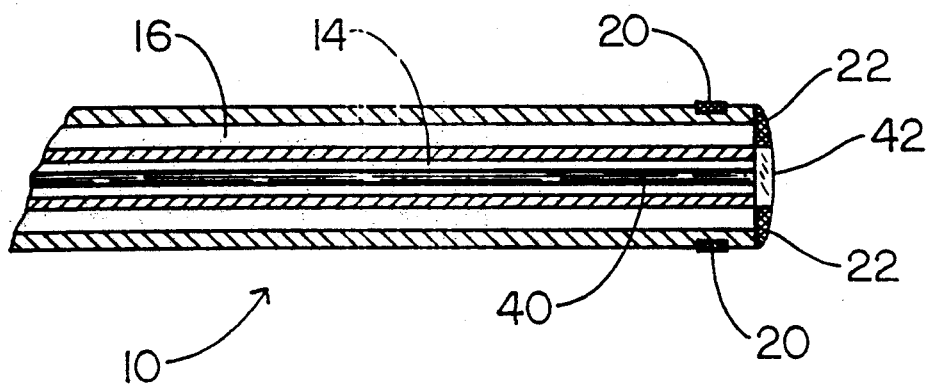
FIG. 11 is a schematic of an embodiment of the catheter of the invention with an optical fiber and light diffuser for laser ablation.
Figure 12:
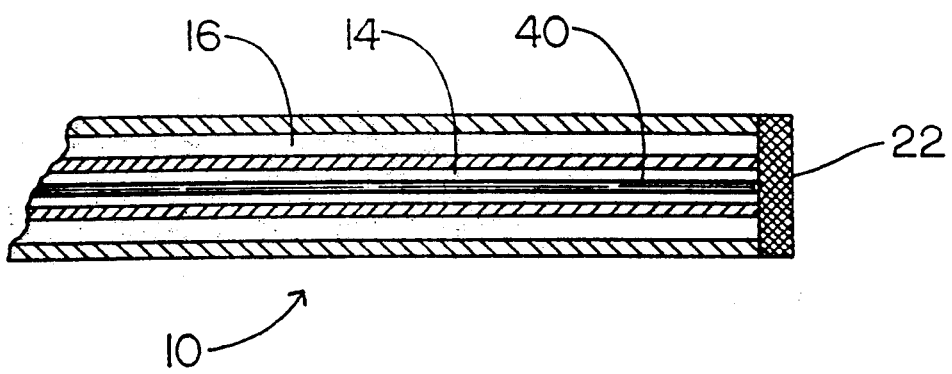
FIG. 12 is a schematic of an embodiment of the catheter of the invention having a heat ablation tip heated by laser energy.

FIG. 11 illustrates another embodiment of the catheter for ice mapping and ablation 10 which incorporates provisions for laser ablation. In this embodiment an optical fiber 40 is passed through the inner lumen 14 to a light diffuser 42 at the distal end of the catheter 10 in the center of the second electrode 22. The optical fiber 40 transmits light energy from a laser positioned at the proximal end of the optical fiber 40 at the proximal end of the catheter body 18. Because the laser light is highly collimated, the light diffuser 42 is used to enlarge the area ablated by the laser energy. Alternatively, the laser light may be used to heat the second electrode 22, as shown in FIG. 12, or a separate thermally conductive element, to a temperature of approximately +80 degrees Celsius for the procedure known as heat ablation. The ice-mapping and laser light or heat ablation procedure is similar to that for radio frequency or direct current ablation, the sole difference being the method of heat generation. As with rf ablation, the second electrode 22 may incorporate stabilization features as depicted in FIGS. 7-10.

The embodiment of FIG. 11 is shown configured with optional first and second electrodes 20 and 22 for electrocardiographic mapping, while the embodiment of FIG. 12 is not, to show the possible variety of configurations for the catheter 10. However, it is also contemplated that the catheter 10 of FIG. 12 be configured with mapping electrodes 20 and 22, and that the catheter 10 of FIG. 11 omit them.

Figure 13:
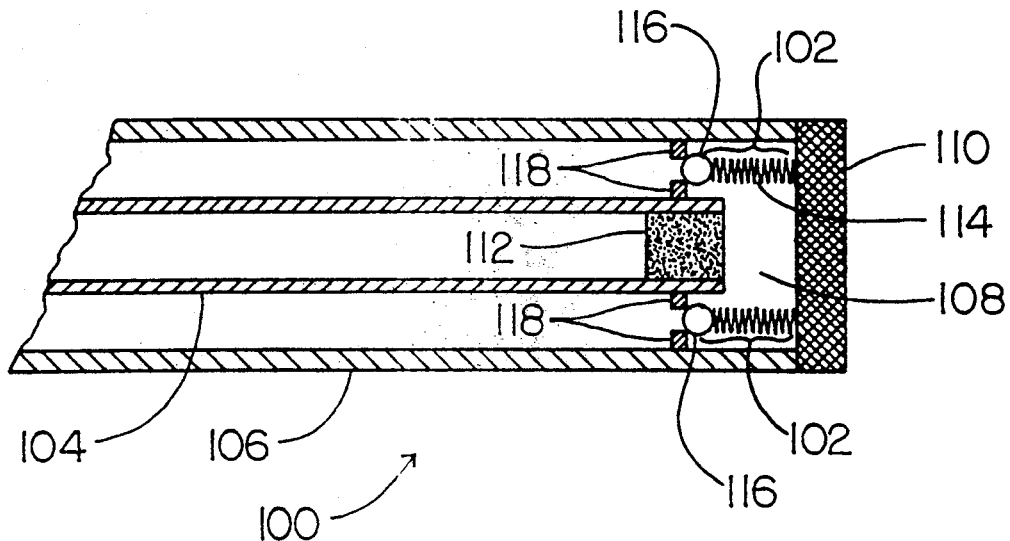
FIG. 13 is a schematic of an embodiment of a cryogenic catheter for cardiac cryosurgery having a ball and spring fluid pressure control device.
Figure 14:
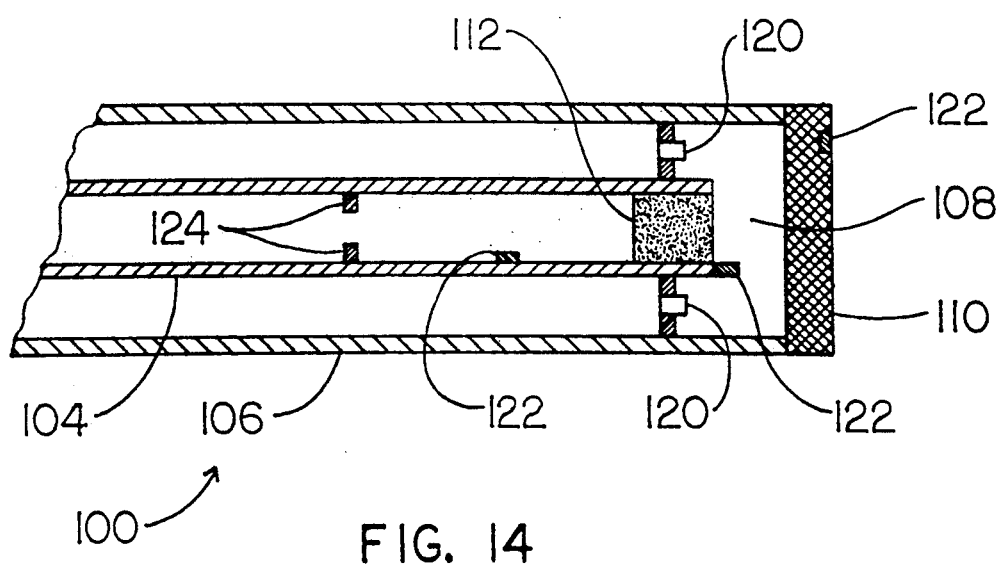
FIG. 14 is a schematic of an embodiment of a cryogenic catheter for endoscopic cryosurgery having an electrically controlled flow control device.

FIGS. 13 and 14 depict two cryogenic catheter embodiments which use cooling for both mapping and ablation. FIG. 13 depicts a cryogenic catheter 100 which uses ball and spring valves 102 to control the pressure of a circulating cooling fluid. The cryogenic catheter 100 is constructed in a manner similar to the catheter for ice mapping and ablation 10 of FIG. 1, and has a first or inner lumen 104 positioned within a second or outer lumen 106. In the exemplary embodiment, a liquid under pressure, such as a chlorinated fluorocarbon at 150 pounds per square inch (psi), is pumped into the outer lumen, thence through ball and spring valves 102 to a boiling chamber 108 proximate a metal cooling tip 110, whereby boiling of the cryogenic fluid cools the tip 110. A micropore filter 112 fills the distal end of the inner lumen 104 to prevent any traces of liquid coolant from entering the inner lumen 104 that serves as the gas return line. By this means boiling is confined to the boiling chamber and the cryogenic liquid does not interfere with the return gas pumping.

The ball and spring valves 102 are arranged about the periphery of the inner lumen 104, and each valve 102 incorporates a helical metal spring or silicone rubber pad serving as a spring 114, pre-loaded to equal or exceed the pressure of the fluid in the outer lumen 106 (e.g., a fluid pressure of 150 psi, and a spring load of 180 psi). The valve 102 may comprise any combination of materials which produce in a liquid tight seal. In a present embodiment, the ball 116 is stainless steel and the seat 118 is polytetrafluorethylene.

In order to cool the tip 110, the fluid pressure in the outer lumen 106 is increased until the ball 116 is displaced from its seat 118, thereby allowing pressurized liquid to enter the expanse boiler chamber 108. The lower pressure in the boiling chamber 108 permits the fluid to vaporize (boil), which causes its temperature to drop and thereby cool the tip 110. Lowering the fluid pressure in the outer lumen 106 to a level below the spring load stops fluid flow into the boiling chamber 108. Because different liquids have different boiling points and vapor pressures, the specific choice of liquid determines the temperature to which the tip 110 is cooled and the required pre-load of the spring value.

The cooling tip 110 that is placed in contact with body tissue to be cooled, may be fabricated from any metal such as surgical stainless steel to ensure bio-compatibility. However, copper which provides superior thermal conductivity, or aluminum may be used, and may be coated with gold, silver, or titanium to preclude an adverse bio-chemical reaction by the body.

Referring to FIG. 14, an alternative embodiment of the cryogenic catheter 100 is shown, wherein actively controlled electrically powered valves 120 place the passive ball and spring valves 102 of FIG. 13 for fluid control. One such valve type is an electric solenoid valve, another is a needle valve. When electrically controlled and powered valves 120 are used, the fluid pressure is held constant within the outer lumen 106. Opening and closing of the valves 120 may be in response to a signal from a remote control unit with allows either manual or automatic temperature regulation or with temperature sensors 122 mounted within the cryogenic catheter 100. The temperature sensors 122 may include at least one thermocouple or thermistor, or other devices well known in the art.

Due to the need for maintaining a uniform temperature at the tip 110, as well as keeping it as cold as possible within the constraints of a given cooling and also to prevent the liquid from entirely filling the boiling chamber and preventing boiling, temperature sensors 122 are especially useful for monitoring tip temperature and for balancing the heat load with the liquid boil off. A temperature sensor 122 is located at the tip 110, in the inner lumen 104, and on the supply side of the filter 112.

Another means of controlling the tip temperature may be achieved by controlling the pressure in the boiling chamber through active pumping or exhausting of the gas, or with in-line flow restriction. By actively pumping out or evacuating the gas from the return gas lumen, the pressure in the boiling chamber 108 is lowered. Because boiling points of liquids decrease with lowered pressure, by this means, the cryogenic liquid in the boiling chamber 108 boils at a lower temperature, thereby lowering the tip temperature further. Conversely, use of a controllable flow restriction device 124 in the exhaust lumen, depicted in FIG. 14, may raise the pressure in the boiling chamber, thereby elevating its boiling temperature and raising the tip temperature.

As previously discussed with respect to the catheter 10 of FIG. 1, the inner and outer lumens 104 and 106, respectively, may be functionally reversed for ease of manufacture or to warm the return gas lumen so as to keep the catheter flexible. The lumens may also be incorporated in the catheter in a non-concentric or side-by-side geometry.

The cryogenic catheter 100 may be rigid or as flexible as the catheter for ice mapping and ablation 10 depending on the desired application. When the catheter 100 is flexible, it may incorporate the steering features disclosed with respect to FIGS. 5 and 6. The catheter 100 may also incorporate the position stabilization devices discussed with respect to FIGS. 7, 8, 9 and 10. Furthermore, the cryogenic catheter of FIGS. 13 and 14 may incorporate the ice mapping and ablation means discussed with respect to FIGS. 1, 3, 4, 11 and 12.

A variety of modifications and variations of the present invention are possible in light of the above teachings. It is therefore to be understood that, within the scope of the appended claims, the present invention may be practiced otherwise than as specifically described hereinabove.

What is claimed:

1. A cryogenic catheter comprising:

a first lumen;

a second lumen;

a valve associated with one of said lumens, said valve regulating flow of a cooling fluid between said first lumen and said second lumen, wherein said valve comprises a ball biased against a ball seat with a biasing means, said ball preventing flow of said cooling fluid through a passage within said ball seat until said cooling fluid exerts sufficient pressure against said ball to overcome bias forces imparted thereon, thereby displacing said ball from said ball seat; and a chamber for permitting said cooling fluid to boil, cool, and thereby chill a tissue cooling surface located proximate said chamber, said cooling fluid introduced into said chamber through said valve by way of said first lumen and exhausted from said chamber via said second lumen.

2. A cryogenic catheter comprising:

a first lumen, having a proximal end and a distal end, concentric with a second lumen, said first lumen permitting a cooling fluid to flow from said proximal end to said distal end, said second lumen, having a proximal end and a distal end, permitting said cooling fluid to flow from said distal end to said proximal end, said first lumen concentric with said second lumen being sufficiently flexible and sufficiently narrow to be inserted into and travel through a cardiac blood vessel without injuring said cardiac blood vessel;

at least one control valve for regulating flow of said cooling fluid from said distal end of said first lumen into a boiling chamber that connects said distal end of said first lumen and said distal end of said second lumen, said boiling chamber permitting boiling of said cooling fluid into a gaseous state, wherein said control valve has an open and a closed state, for permitting said cooling fluid to pass from said first lumen into said boiling chamber when said at least one control valve is in said open state, said at least one control valve responsive to an electric control signal; and a plurality of temperature sensors for producing said electric control signal, including a temperature sensor located within said second lumen; and a cooling surface proximate said boiling chamber, wherein said cooling surface is a thermal conductor.

3. The catheter of claim 2, further comprising a micropore filter positioned within said second lumen to prevent said cooling fluid in a liquid state from exiting said proximal end of said second lumen.

4. The catheter of claim 3, wherein said micropore filter is a plug of glass wool that substantially fills said distal end of said second lumen.

5. The catheter of claim 3, wherein said micropore filter is sponge that substantially fills said distal end of said second lumen.

6. A cryogenic catheter comprising:
   a first lumen, having a proximal end and a distal end, concentric with a second lumen, said first lumen permitting a cooling fluid to flow from said proximal end to said distal end, said second lumen, having a proximal end and a distal end, permitting said cooling fluid to flow from said distal end to said proximal end;
   at least one control valve for regulating flow of said cooling fluid from said distal end of said first lumen into a boiling chamber that connects said distal end of said first lumen and said distal end of said second lumen, said boiling chamber permitting boiling of said cooling fluid into a gaseous state, said at least one control valve comprising:
   a ball seat;
   a ball, matable with said ball seat for forming a fluid tight seal, said ball seat having a passage therein for permitting said cooling fluid to pass from said first lumen into said boiling chamber when said ball is displaced; and
   a biasing means, for biasing said ball toward said ball seat, said biasing means causing said ball to mate with said ball seat until said cooling fluid is pressurized to a predetermined pressure level; and
   a cooling surface proximate said boiling chamber, wherein said cooling surface is a thermal conductor.

7. The catheter of claim 6, wherein said biasing means is a spring.

8. The catheter of claim 6, wherein said biasing means is a compressible pad.

9. The catheter of claim 2, wherein said at least one control valve comprises a needle valve.

10. The catheter of claim 2, wherein said at least one control valve comprises a solenoid valve.

11. The catheter of claim 2, wherein said plurality of temperature sensors comprises at least one thermocouple.

12. The catheter of claim 2, wherein said plurality of temperature sensors comprises at least one thermistor.

13. A cryogenic catheter comprising:
   a first lumen, having a proximal end and a distal end, concentric with a second lumen, said first lumen permitting a cooling fluid to flow from said proximal end to said distal end, said second lumen, having a proximal end and a distal end, permitting said cooling fluid to flow from said distal end to said proximal end;
   a fluid control valve comprising an electrically controlled valve, said fluid control valve having an open and a closed state for permitting said cooling fluid to pass from said first lumen into a boiling chamber when said fluid control valve is in said open state, said boiling chamber connecting said distal end of said first lumen and said distal end of said second lumen, said boiling chamber permitting boiling of said cooling fluid into a gaseous state;
   a cooling surface proximate said expansion chamber, wherein said cooling surface is thermal conductor;
   a micropore filter positioned within said second lumen to prevent said cooling fluid in a liquid state from exiting said proximal end of said second lumen; and
   at least one temperature sensor for producing an electric control signal to command said fluid control valve into said open and said closed states.

14. A cryogenic catheter comprising:
   a first lumen, having a proximal end and a distal end, concentric with a second lumen, said first lumen permitting a cooling fluid to flow from said proximal end to said distal end, said second lumen, having a proximal end and a distal end, permitting said cooling fluid to flow from said distal end to said proximal end;
   a fluid control valve comprising:
   a ball seat;
   a ball matable with said ball seat for forming a fluid tight seal, said ball seat having a passage therein for permitting said cooling fluid to pass from said first lumen into a boiling chamber when said ball is displaced, said boiling chamber connecting said distal end of said first lumen and said distal end of said second lumen, said boiling chamber permitting boiling of said cooling fluid into a gaseous state; and
   a biasing means, for biasing said ball toward said ball seat, said biasing means causing said ball to mate with said ball seat until said cooling fluid is pressurized to a predetermined pressure level;
   a cooling surface proximate said boiling chamber and responsive to thermal activity therein;
   a micropore filter positioned within said second lumen to prevent said cooling fluid in a liquid state from exiting said proximal end of said second lumen; and
   at least one temperature sensor for producing an electric control signal to command said fluid control valve into open and closed states.

15. A method of cryoablation comprising the steps of:
   introducing a cryogenic catheter into a cardiac blood vessel, said cryogenic catheter having a proximal end and a distal end, said cryogenic catheter comprising:
   a first lumen for permitting a cooling fluid to flow from said proximal end to said distal end;
   a second lumen permitting return of said cooling fluid from said distal end to said proximal end;
   a valve associated with one of said lumens, said valve regulating flow of said cooling fluid between said first lumen and said second lumen, said valve responsive to at least one electric control signal;
   a temperature sensor located within said second lumen for providing one of said at least one electric control signal;
   positioning said distal end of said cryogenic catheter at a proposed lesion site;
   introducing a cooling fluid into said first lumen to cool said distal end and thereby cool said proposed lesion site to suppress localized cardiac electrical activity;
   monitoring the temperature within said second lumen with said temperature sensor;
   testing said proposed lesion site for cardiac activity using electrocardiographic mapping means;
   evaluating results of said test to confirm effectiveness of said proposed lesion site; and
   generating a lesion by cryoablation.

16. A method of cryoablation comprising the steps of:
   introducing a cryogenic catheter into a cardiac blood vessel, said cryogenic catheter having a proximal end and a distal end, said cryogenic catheter comprising:
a first lumen for permitting a cooling fluid to flow from said proximal end to said distal end;
a second lumen permitting return of said cooling fluid from said distal end to said proximal end;
a valve associated with one of said lumens, said valve regulating flow of said cooling fluid between said first lumen and said second lumen, said valve responsive to at least one electric control signal;
a first temperature sensor located within said second lumen for monitoring the temperature within said second lumen, said first temperature sensor providing one of said at least one electric control signal;

a second temperature sensor positioned to monitor thermal activity proximate said distal end, said second temperature sensor providing one of said at least one electric control signal;
positioning said distal end of said cryogenic catheter at a proposed lesion site;
introducing a cooling fluid into said first lumen to cool said distal end and thereby cool said proposed lesion site to suppress localized cardiac electrical activity;
monitoring the temperature within said second lumen with said temperature sensor;
testing said proposed lesion site for cardiac activity using electrocardiographic mapping means;
evaluating results of said test to confirm effectiveness of said proposed lesion site; and
generating a lesion by cryoablation.

* * * * *